United States Patent [19]
Haberl et al.

[11] Patent Number: 5,211,179
[45] Date of Patent: May 18, 1993

[54] SYSTEM AND METHOD FOR ANALYZING SELECTED SIGNAL COMPONENTS IN ELECTROCARDIOGRAPHIC SIGNALS, PARTICULARLY LATE POTENTIALS IN ELECTROCARDIOGRAMS

[76] Inventors: Ralph Haberl, Pippingerstr. 124, D-8000 Munich 60, Fed. Rep. of Germany; Hans F. Schels, Behamstr. 21, D-8000 Munchen 21, Fed. Rep. of Germany

[21] Appl. No.: 553,500

[22] Filed: Jul. 13, 1990

[30] Foreign Application Priority Data

Jul. 14, 1989 [EP] European Pat. Off. ........... 89112971

[51] Int. Cl.$^5$ ............................................. A61B 5/0452
[52] U.S. Cl. .................................. 128/702; 364/413.06
[58] Field of Search ............... 128/696, 702, 703, 704; 364/413.06, 413.02, 413.03, 413.05

[56] References Cited

U.S. PATENT DOCUMENTS

| 4,422,459 | 12/1983 | Simson | 128/702 |
| 4,458,692 | 7/1984 | Simson | 128/705 |
| 4,616,659 | 10/1986 | Prezas et al. | 364/413.06 |
| 4,947,857 | 8/1990 | Albert et al. | 128/696 |

FOREIGN PATENT DOCUMENTS 0155670  9/1985  European Pat. Off. .

OTHER PUBLICATIONS

Yamaguchi, T., et al., "Simulation of nonstationary spectral analysis of turbulence in the aorta using a modified autoregressive or maximum entropy (AR/ME) method", Medical & Biol. Eng. & Comput., vol. 25, pp. 553-542 (No. 5 Sep. 1987).
Berbari, E. J., et al., "Methods for Analyzing Cardiac Late Potentials", Computers in Cardiology, pp. 35-40 (IEEE Computer Soc., Oct. 7-10, 1986).
Nikias, C. L., et al., "A New Robust 2-D Spectral Estimation Method and Its Application in Cardiac Data Analysis", ICASSP 82, vol. 2, pp. 729-732 (IEEE Ac. Sp. & Sig. Proc. Soc., May 3-5, 1982).
Haberl, R., "Frequency Analysis of the 4 ECG with Maximum Entropy Method (MEM) versus Fast Fourier Transform (FFT) for Identification of Patients With Ventricular Tachycardia", Circulation, vol. 76, Supp. IV, p. IV-82 (Oct. 1987).

(List continued on next page.)

Primary Examiner—Kyle L. Howell
Assistant Examiner—Kennedy J. Schaetzle
Attorney, Agent, or Firm—Fitch, Even, Tabin & Flannery

[57] ABSTRACT

Disclosed is a system and a method for computer-supported analysis of arrhythmic potentials in ECG signals, particularly those of late potentials. Interference discrimination advantages of frequency domain analysis are combined with temporal localization advantages of time domain analysis to determine the accurate location of arrhythmic potentials. Several small signal segments are selected in an ECG waveform. A determination is made of parameters corresponding to extended signals which closely match fluctuations of each respective small signal, allowing more information is discerned about the small signals than is possible with more conventional techniques. A comparison is made with respect to extended signals rather than small signals. Two autoregressive models are used, the maximum entropy method and adaptive filter determination. Area integrals of the frequency characteristics of small signal segments are recorded successively with respect to the frequency range of the arrhythmic potentials analyzed. The area integrals for first segments are calculated, then the remaining area integrals are calculated to determine the spectral manifestation of the selected signal region. A normality factor is determined as quotient of the summed area integrals of the first and second number of time segments analyzed.

22 Claims, 9 Drawing Sheets

OTHER PUBLICATIONS

Haberl, R., et al., "Comparison of Frequency and Time Domain Analysis of the Signal-Averaged Electrocardiogram in Patients With Ventricular Tachycardia and Coronary Artery Disease: Methodologic Validation and Clinical Revelance", JACC vol. 12, pp. 150–158 (No. 1, Jul. 1988).

Haberl, et al., "Spectral mapping of electrocardiogram with Fourier transform for identification of patients with sustained ventricular tachycardia and coronary artery disease," European Heart Journal, vol. 10, pp. 3161 ∝ 322 (1989).

Cain, M. E., et al., "Fast-Fourier transform analysis of signal-averaged electrocardiograms for identification of patients prone to sustained ventricular tachycardia", Circulation, vol. 69, pp 711–720, (No. 4, Apr. 1984).

Cain, M. E. et al., "quantificaton of Differences in Frequency Content of Signal-Averaged Electrocardiograms in Patients with Compared to Those Without Sustained Ventricular Tachycardia", Am. J. Cardiol., vol. 55, pp. 1500–1505 (Jun. 1, 1985).

Childers, D. G., Ed., Modern Spectrum Analysis, pp. 496 to 498 (IEEE Press, N.Y., 1978). (Explanation of "Burg's Method.").

Friedlander, Benjamin, "System Identification Techniques for Adaptive Noise Cancelling," IEEE Trans. on Acc., Sp., & Sig. Proc., vol. ASSP+, No. 5, pp. 699–709 (No. 5, Oct. 1982).

Papoulis, A., Probability, Random Variables, and Stochastic Processes, pp. 496–498 (McGraw-Hill, 2nd Ed., 1984).

Kalouptsidis, N., et al., "Fast Adaptive Least Squares Algorithms for Power Spectral Estimation," IEEE Transactions on Ac. Sp. & Sig. Proc., vol. ASSP-35, pp. 661–670 (No. 5, May 1987).

Marple, Larry, "A New Autoregressive Spectrum Analysis Algorithm," Transactions of Acc. Sp., & Sig. Proc., vol. ASSP-28, pp. 441–453 (IEEE, No. 4, Aug. 1980).

Broersen, P. M. T., "Selecting the Order of Autoregressive Models from Small Samples," IEEE Transactions on Ac., Sp., & Sign. Proc., vol. ASSP-33, pp. 874–879 (No. 4, Aug. 1985).

Akaike, Hirotugu, "Statistical Predictor Indentification", published on pp. 203–217 of some publication (possible Ann. Inst. Statist. Math, possibly vol. 22 or 23, sometime soon after Dec. 26, 1969, the submission date).

SYSTEM AND METHOD FOR ANALYZING SELECTED SIGNAL COMPONENTS IN ELECTROCARDIOGRAPHIC SIGNALS, PARTICULARLY LATE POTENTIALS IN ELECTROCARDIOGRAMS

BACKGROUND OF THE INVENTION

1. Field of the Invention

The invention relates to electrocardiography and more particularly to computer-supported analysis of selected signal components such as late potentials in electrocardiograms (ECGs), wherein, after preamplification and impedance transformation, signals are incrementally amplified, normalized, digitized, stored in memory, and manipulated by computer to provide temporal and frequency information about selected signal components of waveform segments.

2. Description of the Related Art

After a myocardial infarction, patients are at risk from the occurrence of dangerous disturbances of the cardiac rhythm (ventricular tachycardia). Five to 10% of the post-infarct patients die within one year from sudden rhythmogenically caused cardiac death. Previous methods for identifying this risk group (long-time ECG (Holter ECG) exercise test, ECG at rest) are either not sensitive enough or not specific enough. In the 1970s, minute signal fluctuations (of about 1 to 5 V amplitude) were discovered in the surface ECG during sinus rhythm at the end of the QRS complex, so-called late potentials which occur significantly more frequently in post-infarct patients at risk due to disturbance of rhythm than in patients with a good prognosis.

Verification of these very small potentials reaches the boundary of what is technically possible. Previous methods, utilizing time-domain techniques, use waveform averaging over summation in order to improve the signal/noise ratio. SIMSON's method (reference 1 in Appendix 1), which is the one used most until now, filters the ECG signals bi-directionally by means of a 25-Hz high-pass filter and combines the three channels to form a vector quantity, the filtered QRS complex. The disadvantages of SIMSON's method are:

a) patients with a bundle-branch block must be excluded;
b) definitions of "abnormal" depend on the noise level;
c) definitions are not uniformly handled by various working groups;
d) individual beats cannot be examined;
e) it is impossible to obtain spatial information on one of the three channels; and
f) high-pass filtering can give rise to false results due to filter overshoots and ringing.

More recent methods for detecting late potentials have become known as results of research in the United States and the Federal Republic of Germany was published (references 2 and 3). These methods are based on the fact that late potentials can be detected by spectral analysis of high-frequency signal components in the ST part of an ECG, a region which otherwise has only low frequency components. These methods utilize Fourier transform techniques for power spectrum estimation.

Although frequency domain analysis through the use of Fourier transform techniques avoids some disadvantages of previously used methods which utilize time domain analysis (compare reference 3, in Appendix 1), there are other problems associated with analysis using Fourier transform techniques:

1. The frequency resolution of short waveform segments is poor. However, longer waveform segments cannot be used in the ECG, because ECG sections which are not of interest would be included and thus interfere with the frequency spectrum.
2. It impossible to locate the late potentials temporally in the necessarily long waveform segment examined.
3. Analysis of late potentials is associated with problems in the ST region still containing steep QRS components; this leads to frequency distortions, because steep edges represent high frequency spectral components that interfere with the frequency spectrum.
4. To reduce spectral leakage effects, window functions are artificially imposed on the signal; this further reduces the frequency resolution and can attenuate or extinguish useful signals at the segment boundaries.

Previous methods used time domain techniques to temporally locate small potentials, but those techniques are susceptible to interference. To alleviate interference problems, frequency domain techniques were employed. Regretfully, this is done at the expense of the ability to temporally locate the verified potentials within the waveform analyzed. A relatively large waveform segment is required for Fourier transform techniques, because the frequency resolution attainable from a waveform deteriorates as waveform size is reduced. Moreover, since a Fourier transform can only operate on a finite waveform segment, acquired waveforms must be truncated in the time domain before being transformed into the frequency domain. As a result, frequency information leaks between frequencies causing the frequency representation to be blurred. Windowing is necessary to alleviate these leakage problems, but this is done at the expense of some frequency information, thereby making the resulting frequency domain representation less blurred but more coarse.

Accordingly, a primary aspect of the present invention is to provide spectral and temporal representations of ECG waveforms that are substantially sharper than those obtainable with conventional means.

SUMMARY OF THE INVENTION

The present invention divides a large waveform into small waveform segments, and performs a frequency domain analysis on each small waveform segment. This preserves temporal information, because each analyzed segment can be located within the large waveform. Moreover, the present invention makes frequency analysis of the small waveform segments possible, thereby providing high resolution spectral and temporal representations of large waveform.

The present invention discerns more information from small waveforms than is possible through conventional Fourier transform techniques, because no windowing is necessary for the frequency domain determinations made in the invention. By characterizing short waveforms as longer waveforms, the present invention actually extends the waveforms it operates on, instead of narrowing them, as windowing does. Thus, the present invention preserves and utilizes information that would otherwise be lost through conventional windowing techniques.

Briefly summarized, the present invention contemplates selecting a plurality of time-shifted, overlapping waveform segments in an averaged ECG waveform, each waveform segment being 20 to 70 ms, and preferably 25 to 40 ms long —shorter than the waveform segment lengths customarily subjected to FFT analysis. Next, a generator is designed that can generate an extended or even a continuous waveform which, on the average, closely matches the waveform segment. A separate unique generator is designed for each unique waveform segment. From the generator design parameters or from the generator output, it is then quite easy to generate a frequency domain representation of the output of each generator. No windowing is required, since the generator waveforms are extended. The present invention teaches that these frequency domain representations may then be used to represent the spectrum of the corresponding waveform segment with a substantial increase in spectral and temporal resolution.

The preferred embodiment of the invention is based upon the design of autoregressive filter signal or waveform generators and the utilization of the design parameters of these filters in the calculation of the frequency or power spectrum of the signals that these filter generators are capable of generating. The generator parameters are determined either by means of the so-called "maximum entropy method," also designated and abbreviated as MEM in the text which follows, or by means of the so-called "adaptive filter determination," also designated and abbreviated as AFD in the text which follows; AFD is related to the so-called "fast adaptive forward/backward least-squares method" of generator design. These methods are particularly well adapted for the analysis of ECGs. The present invention teaches methods for calculating the optimum order of the autoregressive model and eliminating interfering low-frequency and fundamental oscillations.

To increase the information content further, inasmuch as the analysis of late potentials in ECGs is involved, not just one segment of the ST region is analyzed but a plurality of segments are analyzed which are mutually offset in time in the ST region. For example, 38 segments which are mutually displaced in time by 2 ms within the ST region can be analyzed together. It is then possible to obtain a high information content in a three-dimensional representation —amplitude versus frequency versus time. This provides temporal information about the cardiac cycle, and more particularly the ST region. From these individual spectra, a "normality factor" is then calculated which specifies whether late potentials are present or not in the ECG of the respective patient.

The particular advantages which are obtained by the invention are:

a) high frequency resolution with short waveform segments;
b) power spectrum estimation without the necessity of windowing;
c) ability to delimit late potentials with respect to noise and other interferences;
d) unambiguous definition of abnormal spectra independent of the noise level; and
e) late potentials that are accurately located within the ST portion.

The system and the method thus combine the advantages of frequency domain analysis with those of time domain analysis without the use of either high-pass filtering or windowing. Short time segments are effectively extended so as to allow the determination of their frequency characteristics as if they were continuously extending waveforms, thus high resolution frequency representations are possible. Also, good separation from interfering influences and a precise definition of "abnormal" is possible. Moreover, significant signal components, for example the late potentials in the ST region in ECGs, can be unambiguously located.

Although the invention is primarily described in application to the detection of late potentials in surface ECGs which are obtained via three bipolar pairs of electrodes, the concept of the invention is not restricted to this specific but currently preferred application. The system and the method according to the invention can also be used for examining other biological signals with regard to special characteristic signal components, for example EEGs, phonocardiographic curves and the like. Neither is there any basic restriction with regard to the type of signal derivation. Thus, for example, derivations from chest wall electrodes can also be used as basic input signals instead of three orthogonal electrode pairs, as can intracardial ECGS. No special range has been established for the frequency analysis of the spectra within reasonable physiologically occurring boundary values, even though it is primarily spectra within the range from 40 to 160 and possibly to 200 Hz which are being considered with regard to the late potentials being discussed.

A particularly interesting field of application of the invention consists in analyzing the QRS complex for rejection diagnosis in heart transplants and in analyzing segments preceding the beginning of the QRS complex, particularly for detecting the so-called His potential. The His potential is produced in the bundle of His at the atrioventricular border and cannot be detected in the conventional ECG because its amplitude is too low. The His spike leads to a higher-frequency content in the frequency spectrum.

In heart transplant patients, frequency analysis of the QRS complex shows an increase in frequency components in the range from 60 to 150 Hz and a decrease in frequency components in the range from 10 to 50 Hz in the ST region during acute rejection reactions.

Compared with the previously used Fourier transform techniques, frequency analysis with autoregressive algorithm of the MEM or AFD, respectively, according to the invention allows these frequency fluctuations in the ECG to be detected and located with high accuracy.

DETAILED DESCRIPTION OF THE PREFERRED EMBODIMENTS

Figure 1:
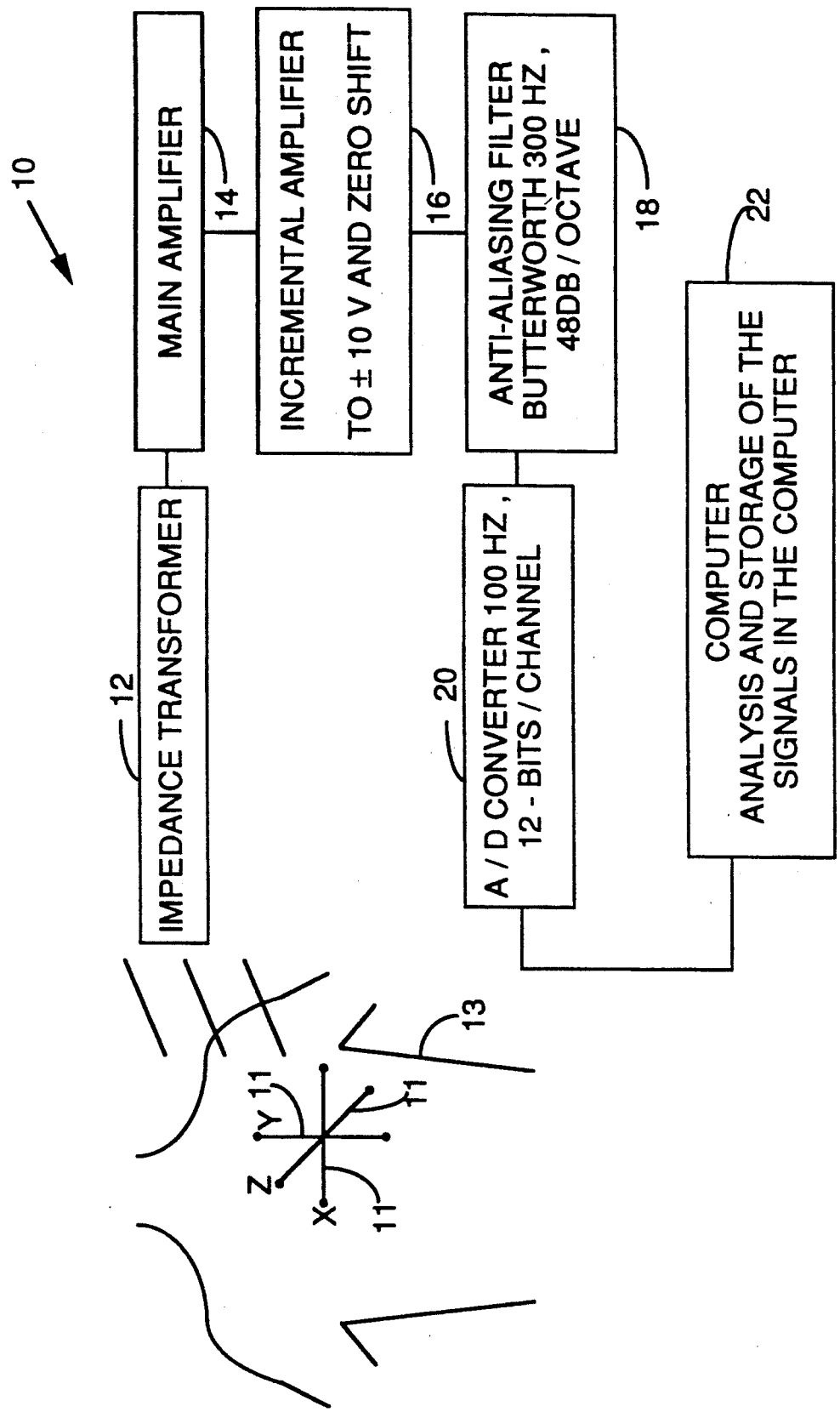
FIG. 1 is an overview block diagram of the apparatus according to the invention for detecting and analyzing late potentials in surface ECGs.

Referring now to the drawing and initially to FIG. 1, a system for analyzing selected signal components in electrocardiographic signals is generally indicated at 10. Orthogonal electrocardiograms are derived from three bipolar pairs of electrodes X, Y, Z 11, connected to human chest 13. An impedance transformer 12 in the immediate vicinity of the electrode pairs minimizes the radiation interference from the environment. In a main amplifier 14, the ECG signals are amplified to ±10 V. Incremental amplifier 16 DC-shift signals allowing full utilization of the input range of an A/D converter 20 (±10 V). The anti-aliasing filter 18 attenuates signal components over 300 Hz prior to sampling. In the tested illustrative embodiment of the invention, the A/D converter 20 operates with a 12-bit resolution and sampling rate of 1000 Hz. The simultaneously recorded ECG signals are stored on a hard disk and processed in the computer 22. During the development work and numerous tests, an industrial 32-bit computer by Hewlett Packard, series 9000 with a clock rate of 16 MHz was very successful. The stored data are analyzed and evaluated as follows:

ECG signals are presented (FIG. 2, Step 202) as 16-bit integer values for a range of $\pm 2^{12}$ ($\pm 2048$). The signals are first computed with the gain factor and preferably specified as real numbers (FIG. 2, Step 204) in miclivolts. The beginning and end of the QRS complex are calculated by autocorrelation. For this purpose, the spatial vector speed (FIG. 2, Step 206) of the ECG is first calculated with the aid of the formula $$v(n) = \sqrt{(x(n+1) - x(n))^2 + (y(n+1) - y(n))^2 + (z(n+1) - z(n))^2}/dt$$

where
v(n) designated the spatial vector speed,
n the data points n=1, ..., N,
dt the sampling rate and
x, y, z the signals supplied by the electrode pairs X, Y, Z.

After a coarse estimation of the end of QRS, for example by the point at which the vector speed drops below 20 mV/s, a QRS signal segment of, for example, 80 ms duration in time, beginning at a point "estimated end of QRS minus 20 ms" passes through the mathematical algorithm of the autocorrelation via convolution. The result is a time series. The time of the maximum of convolution defines the final end of QRS as reference point for the further analysis. The same procedure is used for determining the beginning of QRS.

Figure 2:
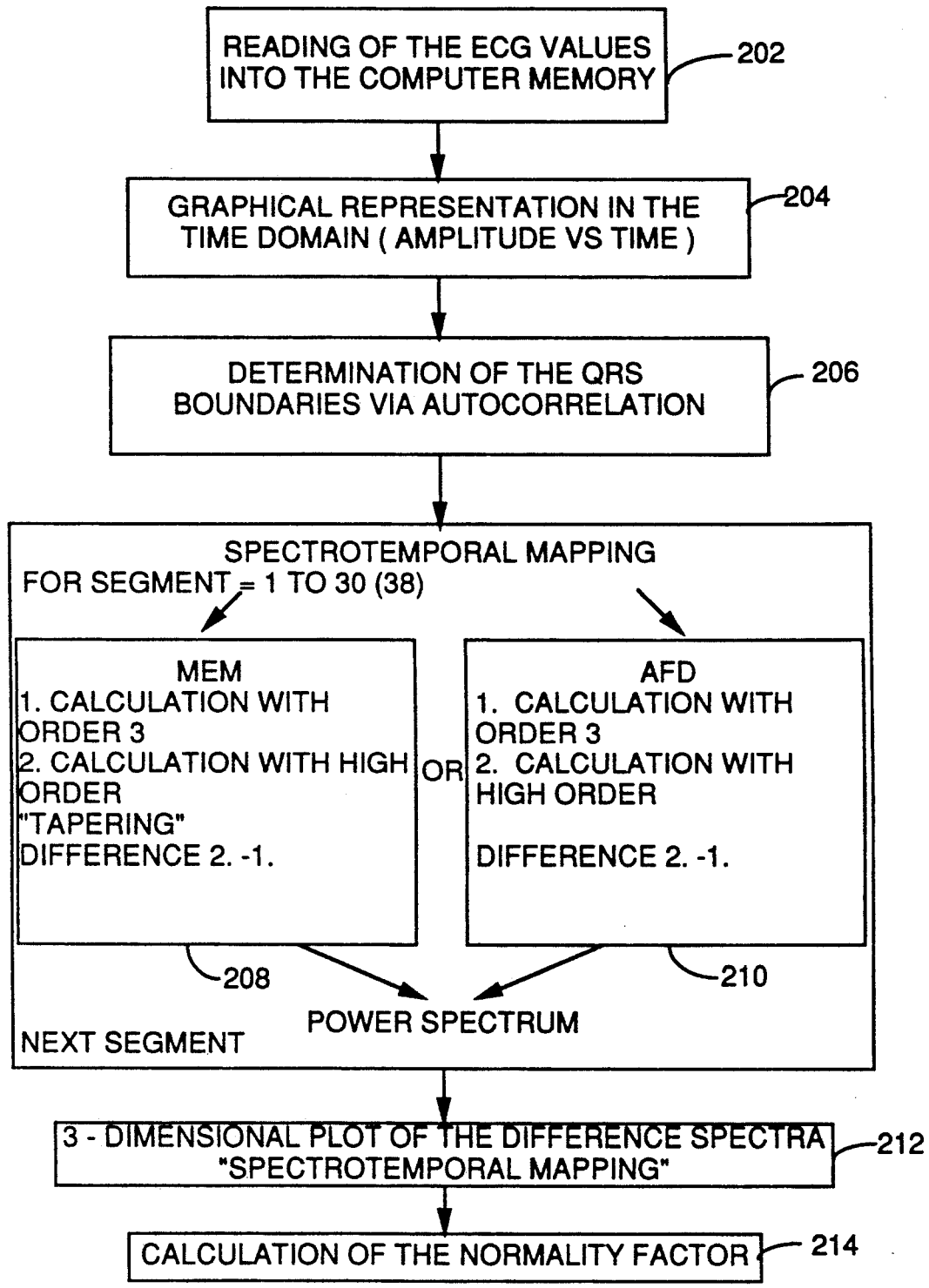
FIG. 2 is a flow chart explaining the individual steps of the signal analysis.
Figure 3:
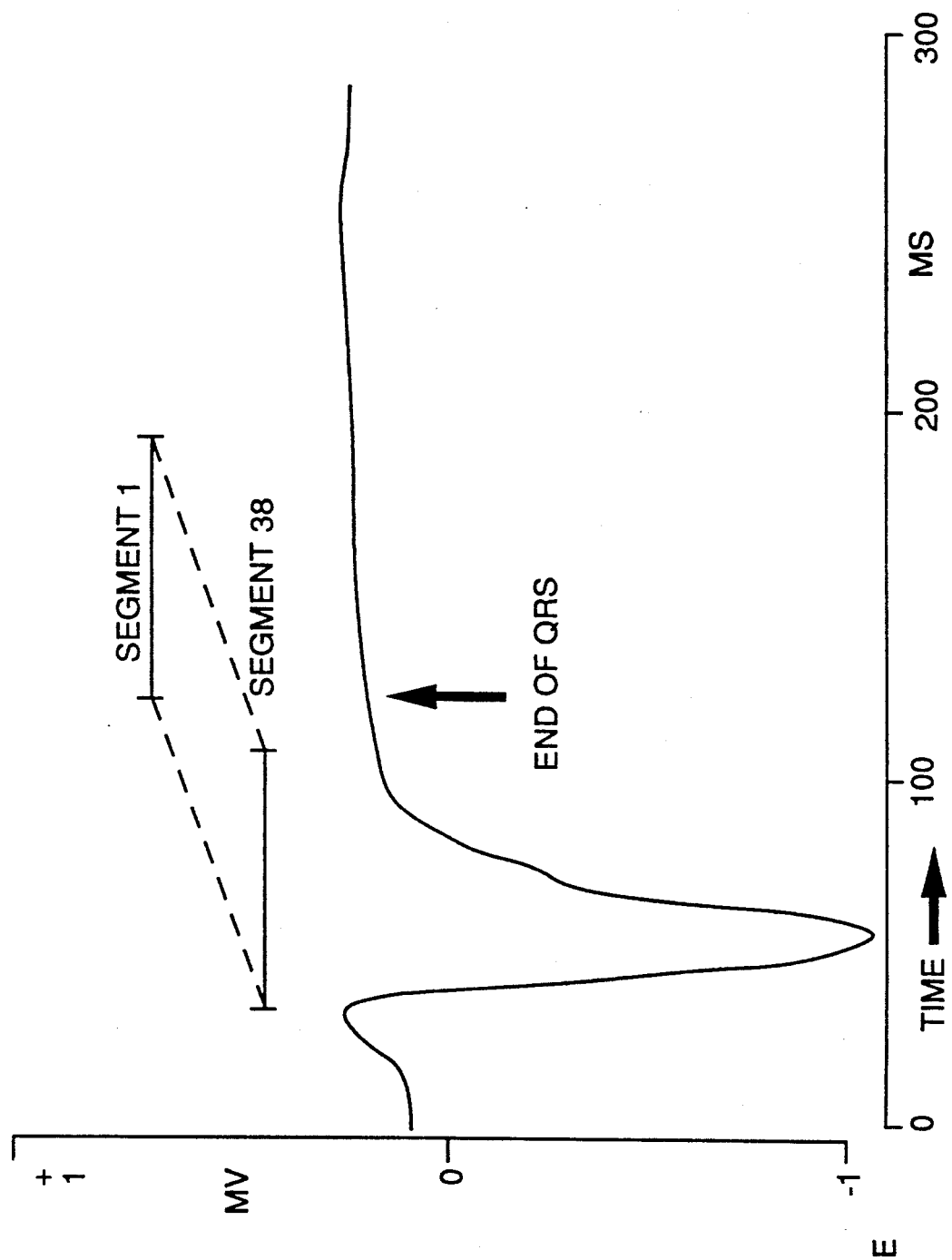
FIG. 3 is a single QRS complex by means of which the operation of the method and of the system according to the invention is explained, illustrating mutually offset time segments within a region of an ECG.
Figure 4A:
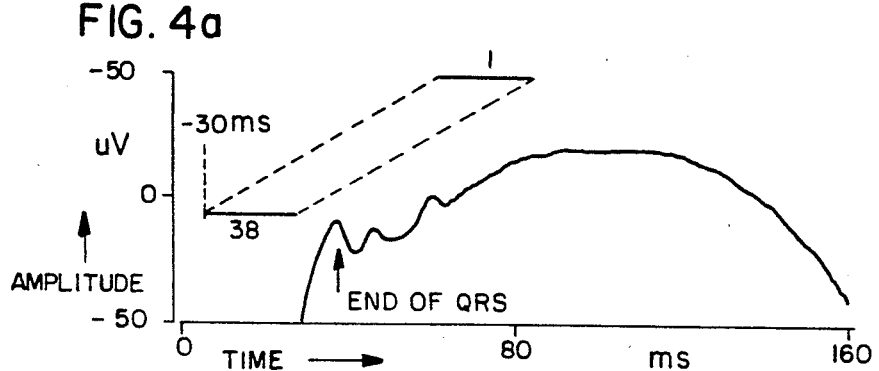
FIGS. 4a–4c comprise three diagrams which illustrate characteristic late potentials for a patient after a myocardial infarction, using the two alternative analysis methods according to the invention.

A particular number of time segments, for example 38 segments is now defined within the ST part. As can be seen in FIG. 3 and FIG. 4a, the first segment begins, for example, 44 ms after the end of the QRS complex; the next ones each begin 2 ms earlier in the cardiac cycle. The 38th segment thus begins 30 ms within the QRS complex. For MEM analysis (FIG. 2, Step 208), the segment length is, for example, 40 ms whilst even shorter segment lengths of, for example, 25 ms are sufficient in adaptive filter determination using the AFD method (FIG. 2, Step 210). The power spectrum is calculated for each of these segments.

The calculation and analysis method effected in the facility according to the invention is called "spectrotemporal mapping" (FIG. 2, Step 212) by the inventors and will be introduced as such as a technical term.

In the text which follows, the two mathematical methods used for the technical solution of the problem demonstrated will be briefly described.

ANALYSIS BY MEANS OF THE MAXIMUM ENTROPY METHOD (MEM)

Calculation of the spectral power density of a time series via the calculation of an autoregressive model (AR model) of a particular order is based on the method described by Burg (1978, lit. 4). The prediction error function is reduced by minimizing the sum of the squared forward and backward errors. At the same time, the so-called Levinson-Durbin algorithm must be satisfied in the recursive calculation of the parameters. The spectrum of the MEM can be represented in a closed form by the equation $$MEM(n) = \sigma^2 \cdot \delta t / \left[ \sum_{m=1}^{M} \cdot a(M,m) \cdot \exp\{-2 \cdot \pi \cdot i \cdot (m-1) \cdot n \cdot \delta t\} \right]^2 \quad (1)$$

where
$\sigma^2$: spectral power density of the white noise;
N number of available data, n = 1, ..., N;
M: model order, m = 1, ..., M;
$\delta t$: sampling rate a(M,m): coefficients of the prediction error filter with length M and a(M,1) = 1.

The forward- and backward-directed prediction errors (errors of the covariance function) of a time series x(n) of length N with respect to time n are given by v(M,n) and r(M,n), M representing the current order of the recursion over the AR parameters. The following holds true:

$$v(M,n) = x(n) + \sum_{m=1}^{M} a(M,m) \cdot x(n-m) \quad (2)$$

and $$r(M,n) = x(n-m) + \sum_{m=1}^{M} a(M,m) \cdot x(n-M+m) \quad (3)$$

a(M,1) = 1, n = 1, ... N, m = 1, ..., M v(M,n), r(M,n) are non-correlated signal sequences (white noise) with the expected value zero and the variance $\sigma^2$ which can be interpreted as root-mean-square error of prediction.

Both errors are calculated via the same coefficients; however, the signal proceeds in opposite directions. This will be briefly explained in the text following:

The available data x(n) are the output or the response word size, respectively, of the unknown linear system S(z), a filter, with $z = \exp[2\cdot\pi\cdot i\cdot f]$, where f = frequency. The signal x(n) to be recorded is generated from incoming white noise via this unknown filter S(z).

The spectrum of x(n) corresponds to the squared filter frequency response and the following holds true:

$$F(f) = |S(s)|^2 \cdot s(x)^2$$

where $|S(z)|^2$: filter power response,
s(x) : power of the white noise at the beginning of S(z),
F(f): spectral power density of the signal x(n),
f: frequency,
z: $\exp[2\cdot]i\cdot f]$.

If the function x(n) can be formed by the filter S(z) from white noise, it must be possible to generate white noise again from the function x(n) by the filter $S^n(z)$, with n = 1, which is the inverse of S(z).

The function S(z) with $$S(z) = 1 / \left( 1 - \sum_{m=1}^{M-1} a(M,m)/z^n \right)$$

is called an all-pole transfer function. The function which is the inverse of this is $S^n(z)$, n = 1, with $$S^n(z) = 1 - \sum_{m=1}^{M-1} a(M,m)/z^n$$

which is called the FIR or all-zero transfer function.

The coefficients a(M,m) are then determined in such a manner that the power of the white noise is minimized at the output when the signal x(n) passes via the inverse filter. This happens by the data or, respectively, the error function in the further recursion, being sent forward and backward through the filter and their respective energies, that is to say the sum of the forward and backward errors, v(M,n) and r(M,n) being reduced. The algorithm used in accordance with the invention here utilizes the property of linear filter systems that a filter which is applied both to the forward- and to the backward-directed signal supplies the same result. The power of forward and backward error function corresponds to the power of the white noise.

For calculating the AR parameters, the sum of the energies of the forward- and backward-directed error function is minimized in accordance with the equation $$\sigma^2(M) = \sum_{n=M+1}^{N} \{v(M,n)^2 + r(M,n)^2\} \quad (4)$$

with the condition that the AR parameters satisfy the Levenson/Durbin recursion $$a(M,m) = a(M-1, M-m) + a(M,M) \cdot a(M-1, M-m) \quad (5)$$

for all orders from 1 to M−1. This requirement is used for generating a stable AR filter (poles inside the unity circle). Minimization is achieved by the derivation of the error terms with respect to a(M,m) being set to zero.

From this follows as expression for the reflection coefficient a(M,m) of the M-th order:

$$a(M,M) = - \frac{2 \cdot \sum_{n=M+1}^{N} \{v(M-1,n) \cdot r(M-1,n-1)\}}{\sum_{n=m+1}^{N} \{v(M-1,n)^2 + r(M-1,n-1)^2\}} \quad (6)$$

The energy of the total error or the variance, respectively, or the dynamic range of the error signal follows as:

$$P(M) = X(m-1) \cdot [1 - a(M,M)^2] \quad (7)$$

The diagrammatic sequence of the MEM algorithm according to Burg can be represented in summary in the following steps:
- initialization:

$$\sigma^2 = \sum_{i=1}^{N} x(i)^2,$$

order = 1
start with order = 1,
calculating the reflection coefficient (Equ. (5))
Levinson/Durbin recursion (Equ. (4), (6))
prediction error determination (Equ. (1), (2)),
incrementing the order and new pass, beginning with the calculation of the reflection coefficient, then calculation of the spectrum (Equ. (1)).

An essential point to be considered when using the MEM for the frequency analysis of the ECG is the choice of the correct order of the autoregressive model, which is represented by the number of AR parameters or of the prediction filter coefficients, respectively. During the development work, it was found that if too low an order was selected, the spectrum is smoothed by a very great amount and the frequency resolution is reduced. Choosing too high an order, in contrast, leads to additional components in the spectrum which do not exist in the original signal.

Known selection methods for determining an optimum order did not bring any fully satisfactory results since none of the known methods met all requirements with respect to spectral resolution, required segment length, tolerable computing time and so forth.

As a very advantageous extension and improvement of the concept of the invention, a procedure was developed in which an optimum determination of the order as termination criterion for the recursion was achieved. According to this extension of the invention, the termination criterion is determined from the combination of three different selection criteria in which, as a rule, the model order is stipulated to be relatively high. The degree of the recursion is established by the criterion which is the first one to satisfy the termination condition.

The termination condition FPE Final Prediction Error Criterion) for the first one of these three criteria is:

$$FPE(m) = \sigma^2 \cdot (n+m)/(n-m)\} < \{FPE(m-1)\},$$
where m = 1, ..., M.

M designates the model order; n is n=1, ..., N; N designates the number of data. Accordingly, the value of a new error criterion for an arbitrary value m must be smaller than its predecessor.

The next criterion for a recursion termination is the condition for a stable filter: the end of the recursion is reached when the calculated filter coefficient becomes greater than 1, that is to say:

$$\text{stop recursion if: } a(M,m) > 1.$$

Possible numeric inaccuracies which can lead to errors are avoided in this way.

If termination is not produced by any of these two criteria, the recursion is stopped after a predetermined upper limit for the number of coefficients of the protection error filter has been reached. This upper limit is calculated in dependence on the number of data within a predetermined data segment; it is determined, for example, at a third of the number of the data set of the root of the current segment length. For the latest termination of the recursion it thus follows that:

$$\text{end of recursion at: } m > 3 \cdot \sqrt[3]{N}.$$

If too high an order is selected in the determination of the said coefficients in MEM for the analysis of the ECG, this can lead to the occurrence of line splitting and frequency shifting. Line splitting is understood to be the splitting of a frequency peak into two or more peaks which are located around the actual frequency. The frequency shifting, that is to say the deviation of a frequency from its original value can be up to 16% of the so-called frequency resolution cell considered in each case. Both phenomena can also be dependent on the starting point, that is to say on the phase relationship and the shape of the curve of the segments considered in each case.

According to a further advantageous extension of the invention, both problems can be largely eliminated by applying a taper function (FIG. 2, Step 208) the calculation of the filter coefficients according to equation (6).

The taper function found to be advantageous has the form:

$$T(m,n) = 6 \cdot (m+1) \cdot (N-n-m+1)/[(N-n+1) \cdot (N-n+2) \cdot (N-n+3)]$$

where
m = 1, ..., M; M: model order and
n = 1, ..., N; N: number of data

It has been found surprisingly that when the relation of the equation for the filter coefficients (equation (6)) is extended by the taper function in the numerator and the denominator, line splitting and frequency shifts no longer occurred even for higher values of the model order M.

Above all, those previously observed interfering impairments of the ECG analysis are eliminated in accordance with the invention which are based on the fact that low-frequency fundamental oscillations, primarily caused by the fundamental oscillation of the S spike of the QRS complex or of the ascending ST part, respectively, cause low-frequency components in the spectra which can have an effect far into the frequency range f>40 Hz, in which late potentials occur. An obvious solution would be a high-pass filtering of the output data; however, as mentioned above, this causes certain disadvantages, particularly signal distortions.

The disadvantages of conventional filtering have been overcome by means of the invention and the fundamental oscillation mentioned is eliminated in accordance with the following method:

The fundamental oscillation, together with a corresponding noise background, is detected at a very low model order number, for example 1, 2 or 3 by the above-mentioned signal analysis. Subsequently, the same section is examined with the optimum order for which the recursion termination criterion is satisfied. A subtraction (FIG. 2, Step 208 and Step 210, and FIG. 9) of the spectrum with the lower model order from the spectrum having the optimum model order on the plane of the calculation of the filter coefficients finally supplies a spectrum having a very low noise level at which the fundamental oscillation is virtually completed reduced.

When the two said improvements of the concept of the invention are simultaneously applied to the calculation of the difference spectra, namely during the calculation of the filter coefficients with optimum model order and in application of the convergence function modification, power spectra can be obtained which produce a much better information content in comparison with conventional methods with Fourier analysis.

ANALYSIS BY MEANS OF THE AFD METHOD

Another method for determining the ECG power spectrum, which can be alternatively applied within the context of the invention, uses in advantageous development of the invention an algorithm which is based on the method which has become known as the "fast adaptive forward-backward least squares" method —an autoregressive method which was presented by N. Kaloupsidis and S. Theodoridis for the first time in 1987 (reference 6, Appendix 1). This method can also be called "adaptive filter determination" (AFD) (FIG. 2, Step 210) in the form modified in accordance with the invention.

The concept of this method is based on the step-by-step adaptation of the filter parameters to the input function with simultaneous minimization of the energies of the forward and backward prediction errors. In contrast to the maximum entropy method (MEM) described above, the input signal is modelled step-by-step from data point to data point with a predetermined number of filter coefficients (fixed model order M).

Analogously to equation (1) in MEM, the power density spectrum of the AFD method is given by:

$$AFD(n) = \sigma^2 \cdot \delta t / \left[ \sum_{m=1}^{M} \cdot a(M,m) \cdot \exp\{-2 \cdot \pi \cdot i \cdot (m-1) \cdot n/\delta t\} \right]^2 \quad (1)$$

where
$\sigma^2$: spectral power density of the white noise;
N: number of available data, n = 1, ..., N;
M: model order, m = 1, ..., M;
$\delta t$: sampling rate
a(M,m): filter coefficients The forward- and backward-directed prediction errors of a time series x(n) of length N at time n are given, similar to the explanation above, by v(M,n) and r(M,n), M again representing the number of filter parameters or the magnitude of the model order, respectively. The following are also true:

$$v(M,n) = x(n) + \sum_{m=1}^{M} J \cdot a(M,m) \cdot x(n - m) \quad (8)$$

and $$r(M,n) = x(n - m) + \sum_{m=1}^{M} a(M,m) \cdot x(n - M + m) \quad (9)$$

v(M,n), r(M,n) are non-correlated signal sequences (white noise) having the expected value of zero and the variance $\sigma^2$ which can again be interpreted as root-mean-square prediction error.

The filter J·a(M,m) is called a forward predictor, with J as so-called exchange matrix which is defined as:

$$J = J(M) = \begin{bmatrix} 0 & \ldots & 0 & \ldots & 1 \\ \cdot & & \cdot & & \cdot \\ \cdot & & \cdot & & \cdot \\ 0 & \ldots & 1 & \ldots & 0 \\ \cdot & & \cdot & & \cdot \\ \cdot & & \cdot & & \cdot \\ 1 & \ldots & 0 & \ldots & 0 \end{bmatrix}$$

The filter a(M,m) is called a backward predictor.

Minimization of the sum of the energies of the forward- and backward-directed error function or filter function provides:

$$\sigma^2(M) = \sum_{n=M+1}^{N} \{v(M,n)^2 + r(M,n)^2\} \quad (10)$$

The AFD algorithm makes no assumption about the signal outside the data range considered or available. The energies of forward and backward prediction errors are simultaneously minimized.

A great advantage of the AFD algorithm is its independence of the start phase of the signal so that line splitting cannot be observed. A high frequency resolution with no significant observed frequency shift even in very short data segments is obtained as a further advantage.

To achieve optimum results within the context of the invention, the correct choice of the number of filter parameters used, that is to say the determination of the optimum order, is also of importance in applying the AFD algorithm. This determination is dependent on the available data and can only be determined with difficulty in advance. In spite of the known AFD algorithm, methods for determining the optimum order are not known. If too low an order is selected, the spectrum is smoothed too much and can mean a reduction in frequency resolution. Choosing too high an order, on the other hand, leads to additional components in the spectrum which are not present in the original signal.

The following selection criterion for determining the optimum order has been particularly successful as an advantageous extension of the concept of the invention:

The algorithm is started with a fixed upper limit (=number of points in a signal section or segment), but a maximum of 50. After each recursion step, it is checked whether the respective last filter errors (forward/backward output) satisfy a particular condition, that is to say are located within a predetermined range. If the errors are outside this range, the recursion is terminated; the current running index of the recursion is stored. Using this current running index, the recursion is subsequently restarted and the filter coefficients are calculated. To check the efficiency and the validity of the order found in each case, a method for assessing the stability of the filter now present, determined by the filter coefficients, is used This checking method is known and has been described in detail by B. Friedlander (reference 5, Appendix 1).

A second possibility for determining an optimum order is given by means of a criterion which has already been described above in conjunction with MEM, according to which $m > 3\sqrt{N}$ is established as upper barrier for an end of the recursion.

The difference spectra are calculated on the basis of similar considerations as has already been described above under MEM.

The results obtained show that the use of even shorter segments is possible with the AFD method, for example segment lengths of only 25 ms, which considerably improves the locating of late potentials in the ST part.

A further advantage of the AFD method lies in the fact that artificial frequency hills occur less frequently and the method is therefore even more specific than MEM in many cases of application as is shown by the information below.

As can be seen from the representations in FIGS. 4 to 7, the power spectra are graphically plotted in a three-dimensional representation, in which the angle of representation can be arbitrarily selected. In FIGS. 4a–4c and 5a–5c, respectively, one pathological and one normal example each is shown for MEM and AFD.

The first patient (FIGS. 4a–4c) suffered from a myocardial infarction with subsequent sustained ventricular tachycardia in the case history.

The second patient (FIG. 5a–5c) also suffered a myocardial infarction but there were no indications of a sustained ventricular disturbance of the rhythm.

Figure 4B:
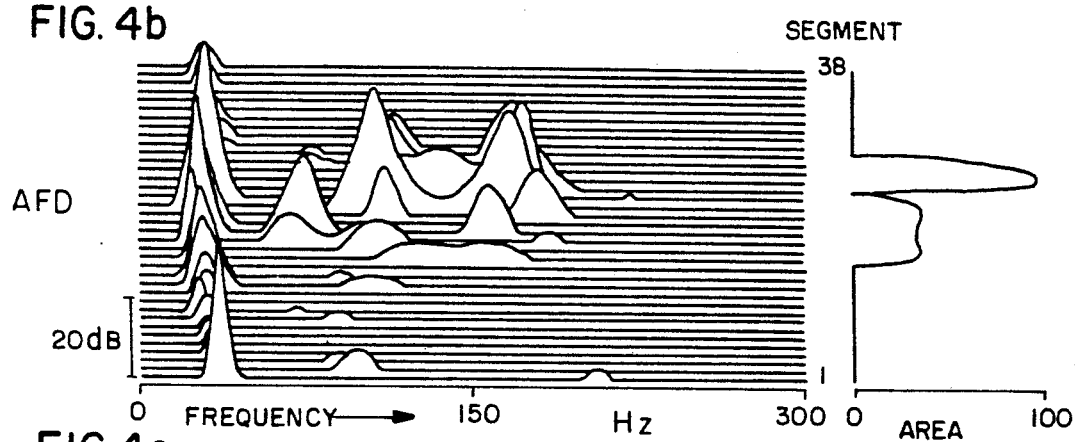
Figure 4C:
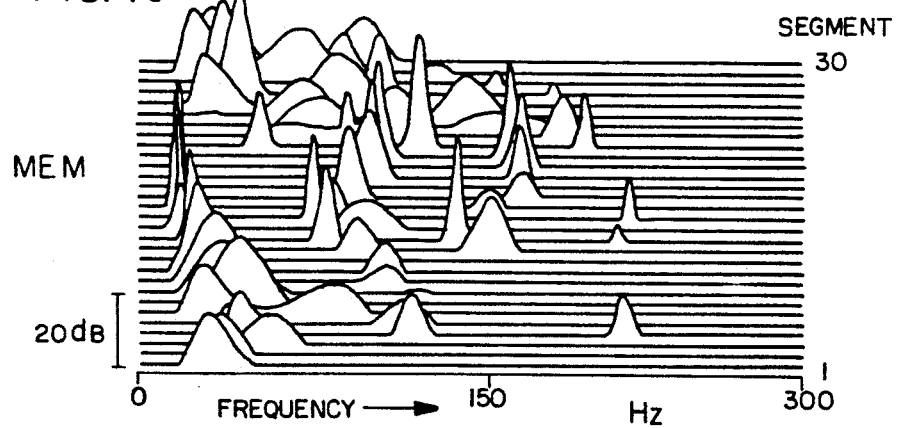
Figure 5A:
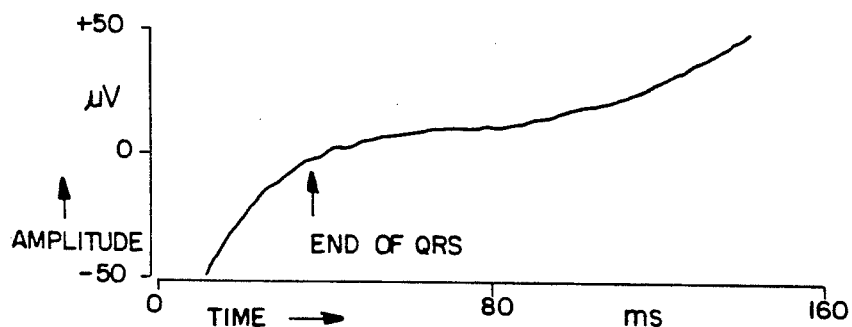
FIGS. 5a–5c comprise three diagrams for a person with a healthy heart, corresponding to the representation according to FIGS. 4a–4c, respectively.
Figure 5B:
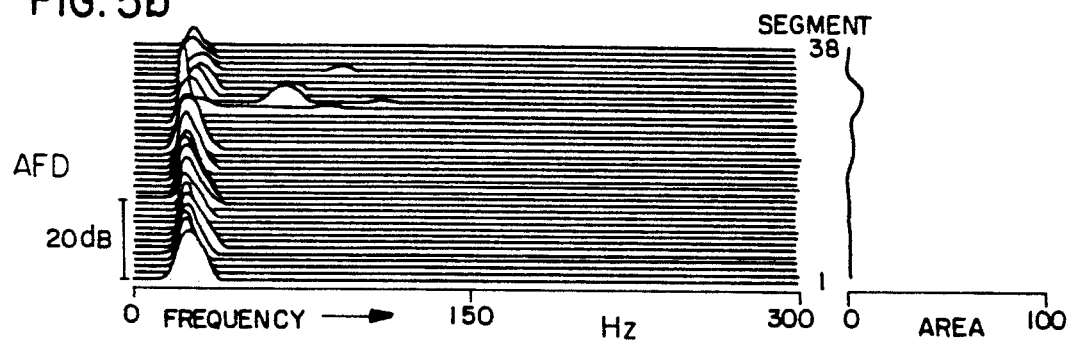
Figure 5C:
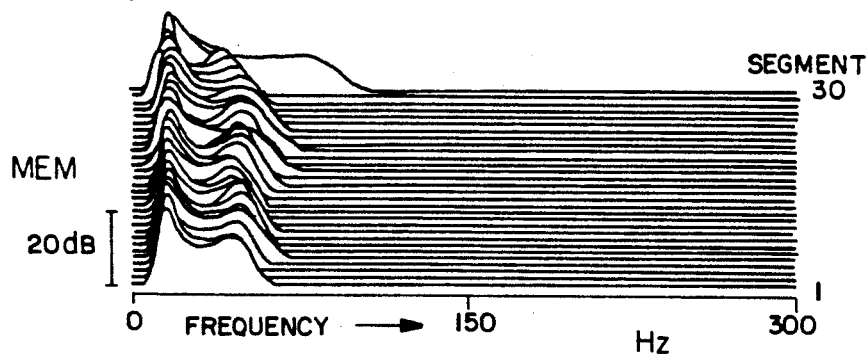

In both cases of FIGS. 4a–4c and 5a–5c, a frequency peak is apparent at low frequency (approximately 15 Hz) which passes through all segments 1 to 38 (AFD) and 1 to 30 (MEM), respectively, and corresponds to the low-frequency fundamental oscillation of the ST part, and can be seen both in the adaptive frequency determination (FIG. 4b, FIG. 5b AFD in each case) and with the maximum entropy method (FIG. 4c, FIG. 5c, MEM in each case). This frequency peak does not interfere with the analysis due to the formation of the difference of the spectra with high and low model order M.

In the region above 50 Hz, higher-frequency components occur in the patient according to FIG. 4a–4c which are mainly located in segments at the end of QRS (FIG. 4c), that is to say in segments 19 to 27 (FIG. 4b, AFD), and in segments 12 to approximately 23 (FIG. 4c, MEM) but are missing segments far outside the QRS complex, that is to say in segments 1 to 18 (AFD) or 1 to 13 (MEM), respectively. This is a characteristic finding for late potentials which can be seen even more clearly in FIG. 4b (AFD). The spectral diagram to the right of AFD clearly shows the summed-together power distribution with a conspicuous power peak in the frequency domain of the late potentials. The normality factor which will be explained in greater detail below, is pathological. The spectra with frequency hills (of corresponding late potentials) can be unambiguously separated and located even more clearly in AFD due to the short segment length in the case of AFD. This provides the possibility of a precise conclusion with respect to the location of the late potentials in the time domain representation (FIGS. 4a and 5a).

The high-frequency components in the segments at the end of QRS are lacking in patients without ventricular tachycardia according to FIG. 5a, 5b, 5c; there is thus no indication of the presence of late potentials.

In distinction from FIGS. 4a-4c and 5a-5c, FIG. 6a-6c shows the analysis of an ECG with the facility according to the invention when interfering influences are present. These also lead to high-frequency components which, however, are present more or less uniformly in all segments. However, these interfering influences drop out in the determination of the normality factor explained in the text which follows.

Figure 6A:
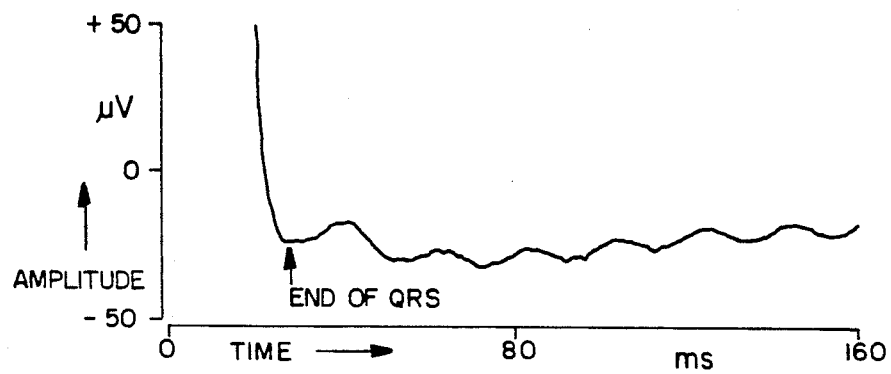
FIGS. 6a–6c comprise three diagrams for explaining how interfering influences of late potentials and method according to the invention, the diagrams also corresponding to the representation according to FIGS. 4a–4c, respectively.
Figure 6B:
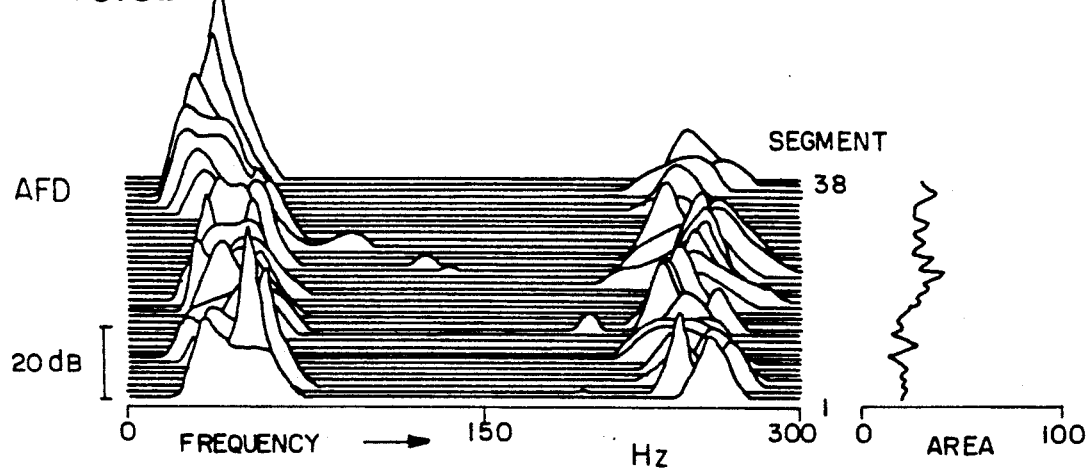
Figure 6C:
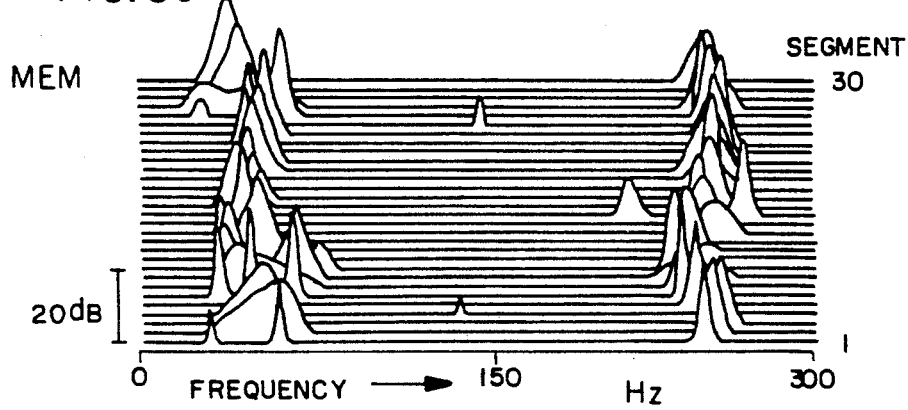

The calculation of the normality factor (FIG. 2, Step 214) is based on the concept that late potentials are only present in segments around the end of QRS but do not occur in segments far outside the QRS complex. In contrast, interfering influences, essentially caused by electrode noise, muscular tremors and mains interference should occur more or less uniformly in all aspects (FIG. 6a-6c). It is known from earlier investigations with Fourier transform (reference 3, Appendix 1) that late potentials are primarily only represented in the frequency range from 40 Hz to 200 Hz.

Using the facility according to the invention, it is first checked in a first step whether frequency peaks with an amplitude of greater than 6 dB occur in the spectra of particular segments, particularly of segments 14 to 30, in the frequency range from 40 to 160 Hz. If this is not so, this finding is not compatible with late potentials; the normality factor is 100%. If, however, corresponding peaks occur, the next step follows.

In step two, the computer checks whether a relevant frequency peak found in the first step only occurs in the selected segments (for example 14 to 30) or whether such a peak appears in the spectra of all segments within a frequency bank of ±10 Hz of the corresponding frequency. If this is so, the spectral representation of an interference signal and not of late potentials must be assumed. The program sequence now returns to step 1 and it is checked whether a further relevant frequency peak is present. If, however, a relevant frequency peak is only located in the segments around the end of QRS and does not exist far outside the QRS complex, the third step now follows.

In the third step, the spectral manifestation of the late potentials is detected. For this purpose, the integral of the area under the frequency curve (compare FIGS. 4b, 4c to 6b, 6c) is calculated in the range from 40 to 160 Hz in the spectra of the previously selected segments, that is to say, particularly, of segments 14 to 30, on the one hand, and in the remaining spectra, that is to say, in particular, spectra 1 to 13, on the other hand.

The normality factor NF (FIG. 2, Step 214) is defined as a quotient, namely $$NF = \frac{(\text{area integral of spectra 1 to 13})}{(\text{area integral of spectra 14 to 30})}$$

With a normality factor NF <30%, significant late potentials must be assumed.

To located the late potentials precisely, the area integral is plotted as a function of all segment numbers, for example of segments 1 to 38, in the range from 40 to 160 Hz (FIGS. 4b and 6b). The start of late potentials is determined as the segment in which the area integral exceeds a particular value. Accordingly, the end of the late potentials is determined as the segment the spectral area of which drops below this limit value.

Figure 7A:
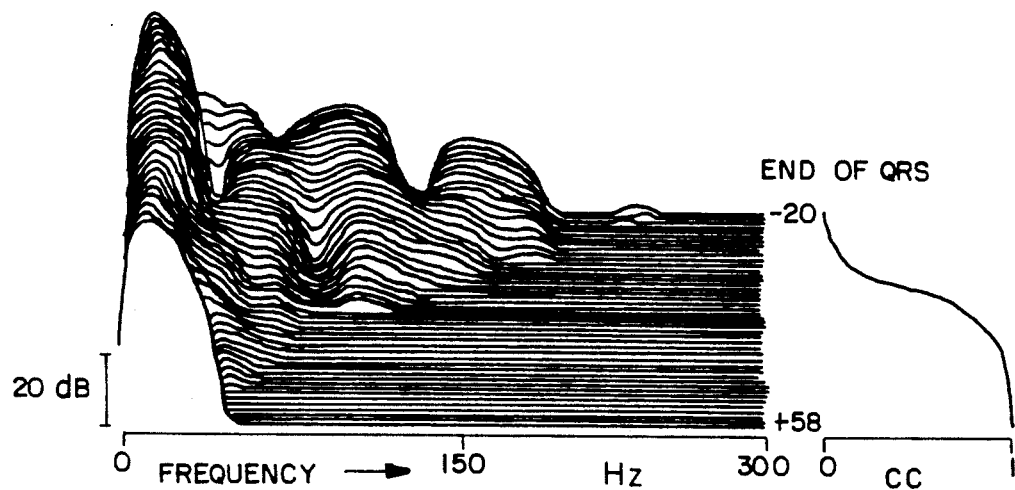
FIGS. 7a–7c comprise three diagrams for comparison with the invention, wherein amplitude/frequency/time diagrams of ST-part sections were subjected to a Fourier analysis according to conventional methods.
Figure 7B:
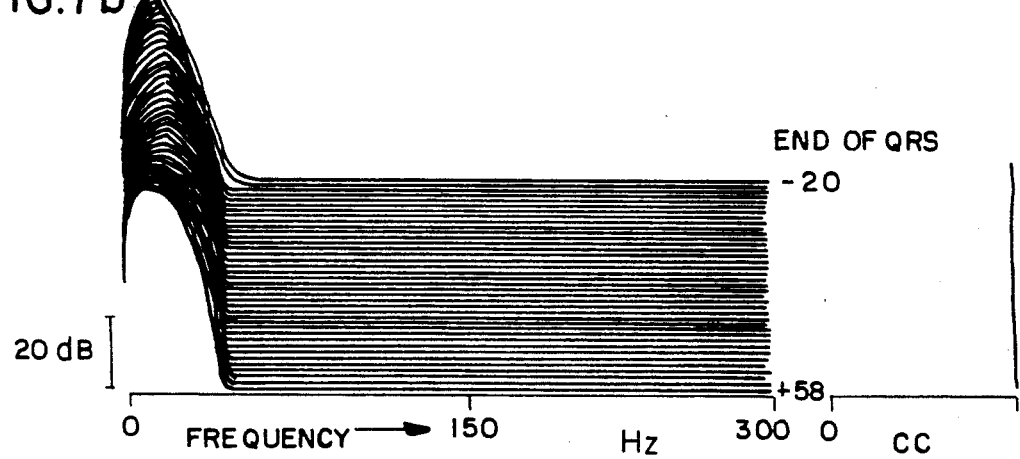
Figure 7C:
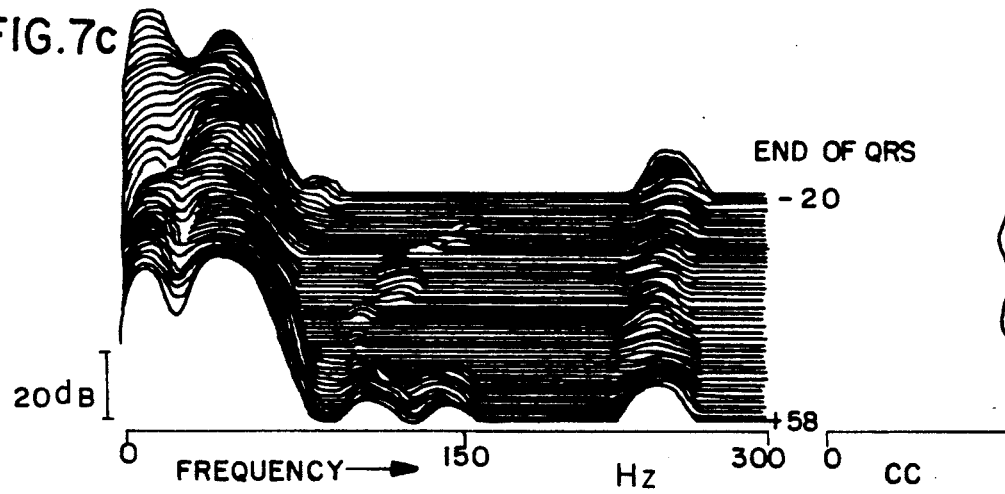

The expert requires no further explanation for the three diagrams of FIGS. 7a-7c which were recorded in familiar manner, but with analog segment-by-segment observation, for comparison with the Fourier analysis of the ST part. FIG. 7a, which was recorded for the same patient with late potentials as in FIG. 4a, clearly shows how much more inaccurate is the possibility of locating late potentials. FIG. 7b would have to be compared with the representation of FIG. 5b and FIG. 7c with the diagram of FIG. 6c.

The present invention can be implemented in a number of different ways, using varying combinations of software and hardware systems. In its essence, the invention contemplates constructing signal generators that generate extended representations of waveform segments too short to be successfully subjected to Fourier transformation. The extended representations preserve the statistics of the short waveform segments, but may be readily analyzed for frequency content without the necessity of windowing or high-pass filtering.

Figure 8:
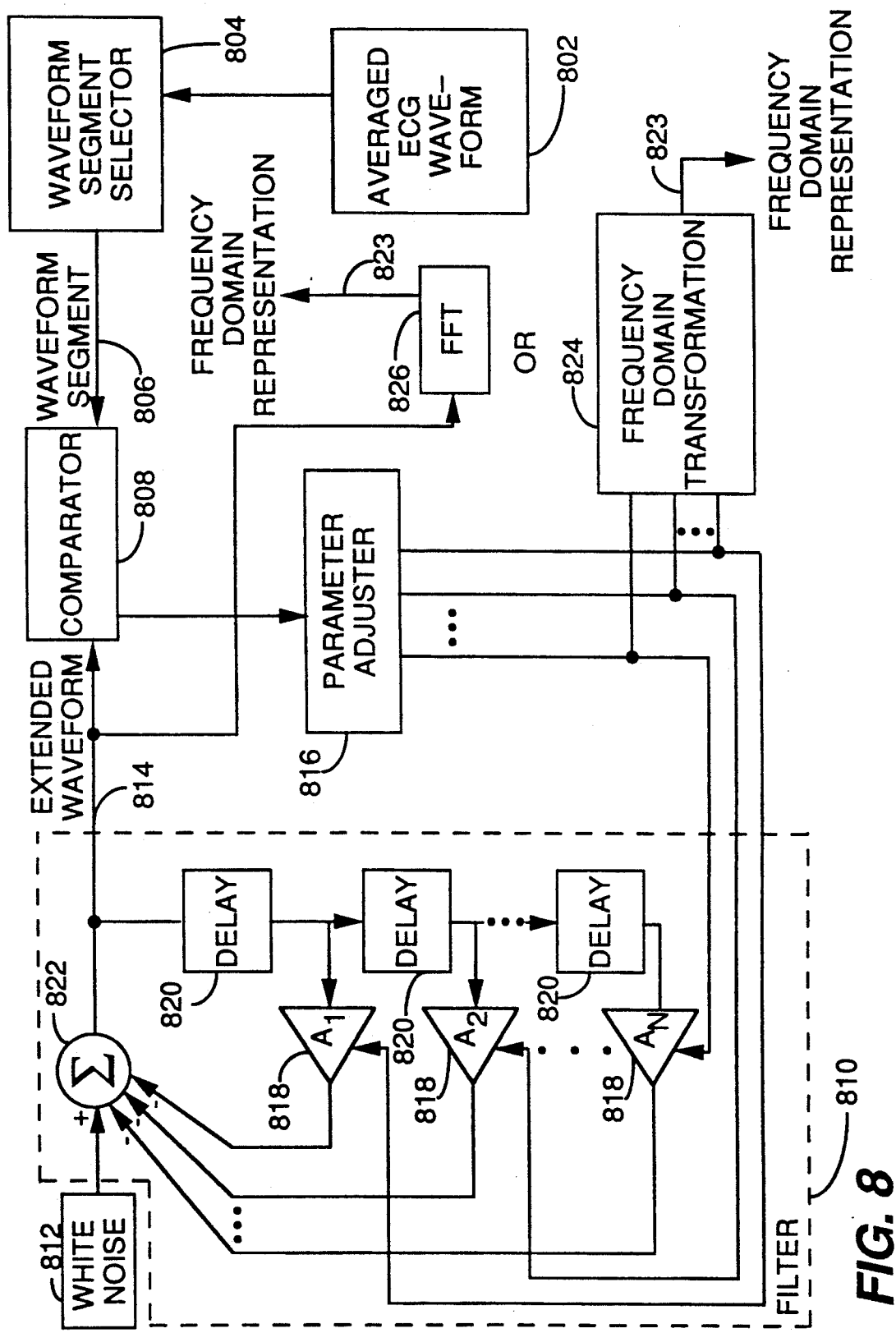
FIG. 8 is a representation of an adaptive filter configuration used to derive an extended waveform which, on the average, matches the selected waveform segments to provide high resolution frequency domain representations of the selected waveform segment.

Referring to FIG. 8, the invention proceeds as follows: The segments of an averaged ECG waveform 802 are selected one-at-a-time by a waveform segment selector 804 which presents an individual WAVEFORM SEGMENT 806 to a comparator 808. Simultaneously, a filter 810 transforms white noise 812 into an EXTENDED WAVEFORM 814 which is also presented to the comparator 808. The comparator 808, using the techniques taught above, either directly or indirectly measures the discrepancy between the two incoming signals or waveforms 806 and 814 and causes a parameter adjuster 816 to adjust filter parameters A1, A2, ... , An 818, and also the number of filter parameters, within the filter 810 to minimize the statistical error detected by the comparator 808. The filter 810 is an autoregressive filter in which the output signal EXTENDED WAVEFORM 814 is fed back through multiple time delays 820, modified by the parameters 818, and summed with the incoming white noise 812 in a summer 822 to give the EXTENDED WAVEFORM 814 which is the filter 810 output signal.

After several iterations of parameter adjustment, as described above, a reasonably good average match between the EXTENDED WAVEFORM 814 and the WAVEFORM SEGMENT 806 is achieved. Then the final step in the process may commence.

The goal is to derive a frequency domain representation of the WAVEFORM SEGMENT 806. Unfortunately, the WAVEFORM SEGMENT 806 is too short in time duration to be transformed by the FFT algorithm. If the WAVEFORM SEGMENT 806 were transformed directly by an FFT transformation, the brevity of the segment would cause the frequency domain representation to be blurred in the frequency direction —smeared or defocused. This problem can be minimized by windowing, but windowing causes information towards the start and end of the segment to be lost, leaving less meaningful information for display and more noise. The segment could be extended in time duration, but then the frequency domain representation would be blurred in the time direction, and it would be difficult to resolve the precise time when a high frequency event occurred —it would appear in the spectrum of many adjoining segments.

To alleviate the above problems, the present invention as configured here provides two different ways to derive the desired frequency representation. Both FFT 826, which takes its input from EXTENDED WAVEFORM 814 and frequency domain transformation 824, which accepts filter parameters from parameter adjuster 816 produce a FREQUENCY DOMAIN REPRESENTATION 823 at their respective outputs. The present invention in its preferred embodiment teaches the latter approach, but the former approach also yields a frequency domain representation which describes the waveform segment.

Figure 9:
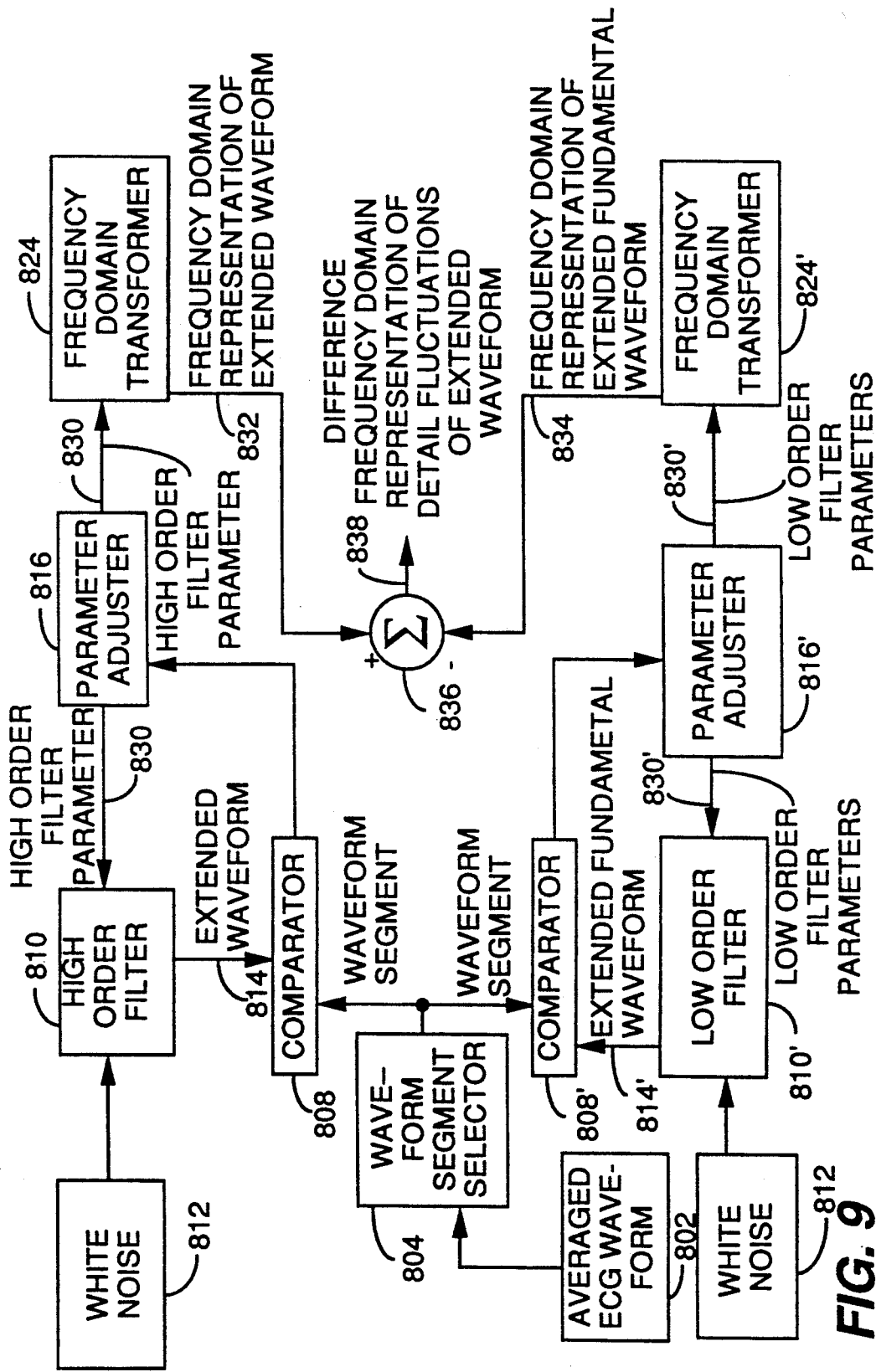
FIG. 9 is a configuration which subtracts the frequency representations of an extended waveform having only fundamental fluctuations from a high resolution extended waveform to provide a difference frequency domain representation of detail fluctuations of the extended waveform.

Referring to FIG. 9, an alternative embodiment of the invention proceeds as follows: The segments of an averaged ECG waveform 802 are selected one-at-a-time by the waveform segment selector 804 which presents the individual WAVEFORM SEGMENT 806 to the comparator 808 and to a second comparator 808'. The filter 810, here referred to as a high order filter, transforms the white noise 812 into the EXTENDED WAVEFORM 814 which is also presented to the comparator 808. Simultaneously, a new low order filter 810' transforms white noise 812 into an EXTENDED FUNDAMENTAL WAVEFORM 814' which is presented to the second comparator 808'. The comparator 808 and the comparator 808', each using the techniques taught above, measure the discrepancy between their respective incoming signal pairs (806 compared with 814 and 814'), thereby causing the parameter adjuster 816 and a second parameter adjuster 816' to each present HIGH ORDER FILTER PARAMETERS 830 and LOW ORDER FILTER PARAMETERS 830' to the high order filter 810 and the low order filter 810', respectively.

Here the goal is to derive a frequency domain representation of the WAVEFORM SEGMENT 806 which is a difference frequency domain representation of the detail fluctuations, rather than the fundamental fluctuations, of the extended waveform. As taught above, an iterative process begins which ultimately results in extended waveforms which, on the average, match the selected waveform segment. While this is clearly the case for high order filter 810, the resulting extended waveform produced by low order filter 810' matches only the fundamental fluctuations of WAVEFORM SEGMENT 806. This is accomplished by limiting the number of filter parameters in the low order filter 810' to a low number such as three or less. Hence the name, low order filter. As taught above, the frequency domain transformation 824 and the frequency domain transformation 824' each operate on filter parameters 830 and 830' to derive the FREQUENCY DOMAIN REPRESENTATION OF EXTENDED WAVEFORM 832 and the FREQUENCY DOMAIN REPRESENTATION OF EXTENDED FUNDAMENTAL WAVEFORM 834. Representations 832 and 834 are presented to summer 836 which subtracts them and presents, at its output, the desired DIFFERENCE FREQUENCY DOMAIN REPRESENTATION OF DETAIL FLUCTUATIONS OF EXTENDED WAVEFORM 838. Representation 838 can then be utilized as a description of the detail characteristics of the WAVEFORM SEGMENT 806 with interfering fundamental fluctuations and fundamental noise attenuated. This provides better discrimination between the diagnostically significant information contained in a waveform segment and other information.

While the configurations of the present invention illustrated by FIG. 8 and FIG. 9 can implemented in software, it should be realized and appreciated that the configurations can also be realized in a partially or completely hardware implementation as well.

APPENDIX 1

Literature References

1. Simson MB., Use of Signals in the Termal QRS-Complex to Identify Patients with Ventricular Tachycardia after Myocardial Infarction. Circulation 1981; 64:235.
2. Cain ME., Amboss HD., Witkowsky FX., Sobel BE., Fast Fourier Transform Analysis of Signal Averaged Electrocardiograms for Identification of Patients Prone to Sustained Ventricular Tachycardia. Circulation 1984; 69:711.
3. Haberl R., Jilge G., Pulter R., Steinbeck G., Comparison of Frequency and Time Domain Analysis of the Signal Averaged Electrocardiogram in Patients with Ventricular Tachycardia and Coronary Artery Disease: Methodologic Validation and Clinical Relevance. JACC 1988; 12:150.
4. Burg JP., Maximum Entropy Spectral Analysis, 37th Meeting of Society of Exploration Geophysicists. In: Modern Spectrum Analysis. Editor Childers DG., IEEE Press, New York (1978).
5. Friedlander B., System Identification Techniques for Adaptive Noise Cancelling, IEEE Transactions on Acoustics, Speech and Signal Processing, Vol. ASSp-30, No. 5 (1982).
6. Kalouptsidis N., Theodoridis S.: Fast Adaptive Least Squares Algorithms for Power Spectral Estimation, IEEE Transactions on Acoustics, Speech and Signal Processing, Vol. 35, No. 5 (1987).
7. Marple, L., A New Autoregressive Spectrum Analysis Algorithm, IEEE Transactions on Acoustics, Speech and Signal Processing, Vol. 28, No. 4 (1980)
8. Papoulis, A., Probability, Random, Variables, and Stochastic Processes, Mc Graw-Hill, Inc., pp. 496–98 (2nd Ed. 1984).

What is claimed is:

1. A system for analyzing selected signal components in physiological measurement signals, comprising:
   means for selecting a portion of a physiological measurement signal to be analyzed;
   means for selecting a plurality of substantially overlapping mutually offset time segments of said portion;
   means for deriving a plurality of low order frequency functions representing the low-band spectral components in each respective time segment;
   means for deriving a plurality of high order frequency functions representing the broadband spectral components in each respective time segment;
   means for deriving a plurality of difference frequency functions by subtracting said low order frequency functions from respective high order frequency functions; and
   means for comparing said difference frequency functions, the comparison indicating detailed analysis of selected signal components in physiological measurement signals.

2. A system in accordance with claim 1 wherein said means for deriving low order and high order frequency functions each comprise means for transforming time domain data values into frequency domain data values.

3. A system in accordance with claim 2 wherein said means for transforming time domain data values into frequency domain data values comprises means for autoregressive computation.

4. A system in accordance with claim 1 wherein said means for comparing comprises:
   means for calculating a plurality of area integrals over a particular frequency range, one for each respective difference frequency function; and
   means for comparing said area integrals, so as to indicate parametric changes associated with said time segments.

5. A system in accordance with claim 1 wherein said portion of a physiological measurement signal to be analyzed is a portion of an electrocardiographic signal having a QRS complex obtained from a patient.

6. A system in accordance with claim 5 wherein said means for selecting a portion of an electrocardiographic signal comprises:
   means for determining a velocity vector function for the electrocardiographic signal;
   means for determining the rate of change of said velocity vector function, said rate of change indicating generally the beginning and end of the QRS complex; and
   means for determining an autocorrelation peak of said velocity vector function in a particular time interval, said autocorrelation peak representing the end of the QRS complex.

7. A system in accordance with claim 6 wherein said means for selecting a plurality of mutually offset time segments comprises means for determining where said plurality of mutually offset time segments are to be positioned relative to the location of said autocorrelation peak.

8. A method for analyzing selected signal components in physiological measurement signals, comprising the steps of:
   selecting a portion of a physiological measurement signal to be analyzed;
   selecting a plurality of substantially overlapping mutually offset time segments of said portion;
   deriving a plurality of low order frequency functions representing the low-band spectral components in each respective time segment;
   deriving a plurality of high order frequency functions representing the broadband spectral components in each respective time segment;
   deriving a plurality of difference frequency functions by subtracting said low order frequency functions from respective high order frequency functions; and
   comparing said difference frequency functions, the comparison indicating detailed analysis of selected signal components in physiological measurement signals.

9. A method in accordance with claim 8 wherein said portion of a physiological measurement signal to be analyzed is a portion of an electrocardiographic signal having a P wave, a QRS complex, and an ST portion obtained from a patient.

10. A method in accordance with claim 9 wherein said time segments are at the trailing edge of the QRS complex and the ST portion for detecting late potentials.

11. A method in accordance with claim 9 wherein said time segments are within the range of the P wave up to the beginning of the QRS complex for detecting potentials of the atrium and of the bundle of His.

12. A method in accordance with claim 9 wherein said time segments are within the range of the P wave, the QRS complex itself and the ST portion for detecting rejection reactions after a heart transplant.

13. A system for analyzing selected signal components in physiological measurement signals, comprising:
   means for selecting a portion of a physiological measurement signal to be analyzed;
   means for selecting a plurality of substantially overlapping mutually offset time segments of said portion;
   means for deriving a plurality of low order frequency functions representing the low-band spectral components in each respective time segment;
   means for deriving a plurality of high order frequency functions representing the broadband spectral components in each respective time segment;
   means for deriving a plurality of difference frequency functions by subtracting said low order frequency functions from respective high order frequency functions;
   means for comparing said difference frequency functions, the comparison indicating detailed analysis of selected signal components in physiological measurement signals; and
   means for outputting a three-dimensional plot of said frequency functions indicating detailed analysis of selected signal components in physiological measurement signals.

14. A system in accordance with claim 13 wherein said portion of a physiological measurement signal to be analyzed is a portion of an electrocardiographic signal having a P wave, a QRS complex, and an ST portion obtained from a patient.

15. A system in accordance with claim 14 wherein said time segments are at the trailing edge of the QRS complex and the ST portion for detecting late potentials.

16. A system in accordance with claim 14 wherein said time segments are within the range of the P wave up to the beginning of the QRS complex for detecting potentials of the atrium and of the bundle of His.

17. A system in accordance with claim 14 wherein said time segments are within the range of the P wave, the QRS complex itself and the ST portion for detecting rejection reactions after a hear transplant.

18. A system in accordance with claim 13 wherein said means for deriving low order and high order frequency functions each comprise means for autoregressive computation.

19. A system in accordance with claim 13 wherein said means for deriving low order and high order frequency functions each comprise means for maximum entropy method (MEM) computation as a method of autoregressie computation for carrying out spectral analysis of the individual time segments.

20. A system in accordance with claim 19 wherein said means for MEM computation comprises: means for deriving a plurality of MEM coefficients; and means for tapering said plurality of MEM coefficients, thereby reducing frequency shifting and splitting-up of the frequency peaks.

21. A system in accordance with claim 13 wherein said means for deriving low order and high order frequency functions each comprise means for adaptive filter determination (AFD) computation as a method of autoregressive computation for carrying out spectral analysis of the individual time segments.

22. A system in accordance with claim 21 wherein said means for AFD computation comprises: means for deriving a plurality of AFD coefficients; and means for predetermining the optimal number of said AFD coefficients.

* * * * *

UNITED STATES PATENT AND TRADEMARK OFFICE
CERTIFICATE OF CORRECTION

PATENT NO. : 5,211,179

DATED : May 18, 1993

INVENTOR(S) : Dr. Ralph Haberl et al.

It is certified that error appears in the above-indentified patent and that said Letters Patent is hereby corrected as shown below:

Other Publications, p. 2, column 1, line 11, change 3161 $\propto$ 322 to --316-322--.

Other Publications, p. 2, column 1, line 15, after "pp" insert --.-- (period).

Other Publications, p. 2, column 1, line 16, change "quantificaton" to --Quantification--.

Other Publications, p. 2, column 2, line 3, change "ASSP+" to --ASSP-30--.

Other Publications, p. 2, column 2, line 14, change "of" to --On--; and change "Acc." to --Ac.,--.

Other Publications, p. 2, column 2, line 25, change "possible" to --possibly--.

At column 1, line 29, change "5 V" to --5 $\mu$V--.

At column 1, line 44, change "SIMPSON's" to --SIMSON's--.

At column 2, line 8, after "It" insert --is--.

At column 4, line 20, change "ECGS" to --ECGs--.

At column 4, line 67, after "potentials" insert --can be unambiguously distinguished by means of the system--.

At column 5, line 47, change "miclivolts" to --millivolts--.

UNITED STATES PATENT AND TRADEMARK OFFICE
CERTIFICATE OF CORRECTION

PATENT NO. : 5,211,179

DATED : May 18, 1993

INVENTOR(S) : Dr. Ralph Haberl et al.

It is certified that error appears in the above-indentified patent and that said Letters Patent is hereby corrected as shown below:

At column 6, line 39, change "$\sum_{m-1}^{M}$" to --$\sum_{m=1}^{M}$--.

At column 6, line 46, begin new line with "a(M,m):"

At column 6, line 62, change "$\sum_{m-1}^{M}$" to --$\sum_{m=1}^{M}$--.

At column 6, line 66, change "$\sum_{m-1}^{M}$" to --$\sum_{m=1}^{M}$--.

At column 7, line 16, change "S(s)" to --S(z)--.

At column 7, line 20, change "s(x)" to --s(x)$^2$:--.

At column 7, line 24, change "exp[2·]i·f]" to --exp[2·π·i·f]--.

At column 7, line 40, change "$\sum_{m-1}^{M}$" to --$\sum_{m=1}^{M}$--.

UNITED STATES PATENT AND TRADEMARK OFFICE
CERTIFICATE OF CORRECTION

PATENT NO. : 5,211,179

DATED : May 18, 1993

INVENTOR(S) : Dr. Ralph Haberl et al.

It is certified that error appears in the above-indentified patent and that said Letters Patent is hereby corrected as shown below:

At column 7, line 65, change "Levenson" to --Levinson--.

At column 8, line 5, change "as" to --an--.

At column 8, line 17, change ") (m-1)" to --P(M-1)--.

At column 8, line 63, change "Final" to --(Final)--.

At column 8, line 67, change "$\sigma^2$" to --{$\sigma^2$ --.

At column 9, lines 16-17, change "protection" to --prediction--.

At column 10, line 18, change "completed reduced" to --completely reduced--.

At column 10, lines 36-37, change "Kaloupsidis" to --Kalouptsidis--.

At column 10, line 57, change "$\overset{M}{\underset{m-1}{\Sigma}}$" to --$\overset{M}{\underset{m=1}{\Sigma}}$--.

At column 11, line 5, change "$\overset{M}{\underset{m-1}{\Sigma}}$" to --$\overset{M}{\underset{m=1}{\Sigma}}$--.

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

At column 11, line 9, change " $\sum^{M}$ " to -- $\sum_{m=1}^{M-1}$ --.

At column 12, line 10, after "used" insert --.-- (period).

At column 12, line 41, change "FIG." to --FIGS.--.

At column 12, line 50, after "5b" insert --,-- (comma).

At column 12, line 56, change "FIG." to --FIGS.--.

At column 13, line 10, change "FIG." to --FIGS.--.

At column 13, line 12, change "FIG." to --FIGS.--.

At column 13, line 26, change "FIG." to --FIGS.--.

At column 13, line 67, change "located" to --locate--.

At column 16, line 4, after "can" insert --be--.

At column 16, line 11, change "Termal" to --Terminal--.

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

Appendix 2

Program for calculating the filter coefficients according to MEM

```
'
'
'
Integer Ord, PBest, Start, SegSize, Taper, Wik, Nord, Nu, W
Integer I, L, P, T
'
'Ord, PBest : maximum or optimum order, resp.
'Start, SegSize : starting point and segment length of data
'Taper, Wik, Nord, Nu : variable for calculating the taper function
'W : variable for dimensioning required fields (W=250)
'I, L, P, T : loop, run or auxiliary indices
'
'
Real Nom, Den, Ena, Ene, Prod, Produc, Startaic, Relerr, Eno
Real G
'
'Nom, Den : numerator and denominator in the calculation of
'coefficients
'Ena, Ene : mean value and variants of the input signal
'Prod, Produc : current value or final value of filter output
'Startaic : starting value of filter output
'Relerr : barrier for termination criterion
'Eno : auxiliary variable
'G : filter coefficient
'
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
Allocate Fdu(W), Fpe2(W), Ad(W), Help(W)
'
'Fdu : data (transfer from main program as signal (*))
'Fpe2 : relative error (termination criteria)
'Ad : filter coefficients
'Help : auxiliary field for buffer or restorage
'
'
'Characters : AK$
'
'AK$ : automatic search for optimum order (yes/no)
'
'
'
'******************* START ********************
'
'
'___ Restorage of data to field Fdu
'
MAT Fdu= signal (Start:Start+SegSize-1)
'
'
'___ Calculation of maximum order
'
Ord=INT(3*SQR(SegSize))
'
'___ Calculation of mean value and variance
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
Ena-SUM(Fdu)/SegSize
'
MAT Fdu= Fdu-(Ena)
MAT Help= Fdu . Fdu
Eno=SUM(Help)/(SegSize-1)
Ene=SQR(Eno)
'
'___ Calculation of first filter output
'
Startaic=(SegSize+1)/(SegSize-1)/Eno
'
'___ Preallocation of individual variables
'
RESTORE 10
10 DATA 1,1,1,0,1,2
READ Produc, Prod, PBest, P, Wik, Nu
'
' ___ r_r_r_r_r__recursion branch destination _r_r_r_r_r_
100 P=P+1
    L=P+1
    Nom=0
    Den=0
'
'___ Calculation of filter coefficients
'
FOR I=L TO SegSize
'
'      ___ Calculation of taper function
        '
        'Possible : taper of order : 0, 2, P
        'Taper of P-th order attenuates more than
        '2nd-order taper
        '
```

UNITED STATES PATENT AND TRADEMARK OFFICE
CERTIFICATE OF CORRECTION

PATENT NO. : 5,211,179  p. 8 of 19
DATED : May 18, 1993
INVENTOR(S) : Dr. Ralph Haberl et al.

It is certified that error appears in the above-indentified patent and that said Letters Patent is hereby corrected as shown below:

```
    IF Taper=1 THEN Nu=P
    IF Taper<>0 THEN
        (this is followed by further program steps)
    '
    Nom=Nom ...
    Den=Den ...
NEXT I
'
G=DROUND(2*Nom/Den,8)
'Enter new coefficient in field Fdu(*)
Fdu(P)=G '
'
'___ Calculation of new filter output
'
Produc=Produc*(1-G*G)
'
'___ Levinson/Durbin recursion :
'    Filter coefficient update
'
IF P>1 THEN
    L=INT(P/2)
    FOR I=1 TO L (further program steps)
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
     ...
   NEXT I
END IF
'
' ___ Criterion for termination of recursion
'     ... (further program sequence)
Relerr= ...

IF P>1 AND AK$='J' THEN
       ...

END IF
IF P=1 OR AK$='N' THEN
     PBest=P
     Prod=Produc
END IF
'
'Termination if P has reached maximum order Ord
'
IF P<Ord THEN
'
'Calculation of new error filter function:
'  "Update of forward and backward functions"
'
L=P+1
FOR I=SegSize TO L STEP -1

...
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
NEXT I
Ad(P)=G
GOTO 100
END IF
'
'End of coefficient calculation,
'  Coefficients are entered in field Fdu(*)
'

'___ Calculation of spectrum
'
'
'___ Editing for transferring the field to FFT
'
MAT Help=Fdu/(-1)
REDIM Fdu(0:Ord)
MAT Fdu(0:Ord-1)= Help(1:Ord)
Fdu(0)-1
'
'
'___ Transfer to FFT
'XA, YA : auxiliary fields of FFT
'
Fft_Size=512
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
CALL FFT(XA, YA, Fdu, Fft_Size)
'
Prod=2*Prod/Fft_Size
L= Fft_Size DIV 2
'
'___ Spectrum MEM(*)
'
FOR I=1 TO L
    MEM(I)=Prod/(XA(I)^2+YA(I)^2)
NEXT I
'
' *** End ***
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

APPENDIX 3
Program for calculating the filter coefficients according to AFB

```
'
'
'
Integer Ord, PBest, Start, SegSize, W
Integer I, J, K, K_10, Merk
'
'Ord, PBest : maximum or optimum order, resp.
'Start, SegSize : starting point and segment length of data
'W : variable for dimensioning necessary fields (W=250)
'J : running index via loop 1 for present signal
'I : running index via order
'K, K_10, Merk : loop and auxiliary indices
'
'
Real Ena, Ene, Ene_merk, Enep, Prod, Relerr
Real Ec1, Ec2, Lw, Ew, Egw, Eu, Egu, Lu
Real Sum, Sum_1, K1, K2
Real Lm_11, Lm_22, Lm_12, Lm_21, B_11, B_22, B_12, B_21, Ek
'
'Ena, Ene : mean value and variance of the input signal
'Ene_merk : starting value of the filter output
'Enep, Prod : current value or final value of the filter output, resp.
'Relerr : barrier for termination criterion
'Ec1, Ec2, Lw, Ew, Egw, Eu, Egu, Lu, Sum, Sum1, K1, K2 :
'  Auxiliary variables for filter output or variance
'  calculation, resp., of the forward and backward error
'  filter functions
'Lm_11, Lm_22, Lm_12, L_m21, B_11, B_22, B_12, B_21, Ek:
'  Auxiliary variable for calculating the error filter functions
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
'
Allocate Ad(W), Fd(W)
Allocate Xa(W), Ya(W)
Allocate Fpe(W), Fpe2(W), Neu(W)
Allocate Help(W), Help1(W), Help2(W)
'
'Fdu : data (transfer from main program as signal (*))
'Ad : data, in reverse order (from 1 to Ord in each case!)
'Fd : filter coefficients
'Xa, Ya : Forward and backward error filter functions, resp.
'Fpe : Total error function
'Fpe2 : Error sum : forward and backward, auxiliary field
'Neu : relative error (termination criteria)
'Help, Help1, Help2 :
'    Auxiliary fields for buffer or restorage
'
'
'
'
'
'    ***************** START *****************
'
'
'___ Restorage of data to FDU field
'
MAT Fdu=Signal(Start:Start+SegSize-1)
'
'___ Determining maximum order
'
Ord=50
If Ord>SegSize Then Ord=SegSize
'
'___ Calculation of mean value and variance
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
Ena=SUM(Fdu)/SegSize
'
MAT Fdu=Fdu-(Ena)
MAT Help=Fdu.Fdu
Ene=SQR(SUM(Help)/(SegSize-1))
'
'___ Restorage and preallocation of individual variables
'
Ene_merk=Ene
Enep=Ene
'
RESTORE 10
10 DATA 1,1,0,0,0,0
READ Lm_11,Lm_22,Lm_12,Lm_21,Eu,Egu
'
'
'
'   ___r_r_r_r_r__ recursion ___r_r_r_r_r___
'
For J=1 To SegSize
'
'
'___ Step 1, Total error function
'
    For I-1 To Ord
       Fpe(I)=Ya(I)+Xa(I)*Egu
    Next I
'
'
'___ Step 2, forward error function
'
Sum_1=0
K_10=Ord+1
For I=1 To Ord ...
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
   ...
Next I
Lw=Lm_22-Egu*Eu
Ew=Sum_1
Egw=Ew/Lw
Sum=0
For I=1 To Ord ...
   ...
Next I
'
'
'
'___ Step 3, backward error function
'
For I=1 To Ord ...

...
Next I
K1=-(Sum+Fdu(J))/Ene
K_10=Ord+2
For I=1 To Ord ...

...
NEXT I
Fpe2(1)=K1
K2=Fpe2(Ord+1)
For I=1 To Ord
    Ya(I)=Fpe2(I)-Fd(I)*K2
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
NEXT I
'
'
'_____ Step 4, calculation of filter coefficients and
'update of error filter functions
'
Ec1=-Ene*K1
Ec2=-Ene*K2
Lm_11=   ...
Lm_22=   ...
K_10=Ord+1
For I=1 To Ord-1
    ...

Next I
Ad(1))=Fdu(J)
Sum=0
Sum=Dot(Ad,Xa)
'
'
'Determination of optimum order
'
Relerr=0
If Ya(Ord)<>0 Then Relerr=1-Sqr(Xa(Ord)/Ya(Ord))
Neu(J)=0
If Relerr>0 Then ...
    ...
            'Termination criterion satisfied
End If
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl et al.

It is certified that error appears in the above-indentified patent and that said Letters Patent is hereby corrected as shown below:

```
'End of determination of optimal order
'Termination if maximum order Ord has been determined
'followed by restart of recursion with this order
'
'
Lm_21=-Sum
Lm_12=Lm_21
Eu=-Lm_12
Lu=Lm_11
Egu=Eu/Lu
'Inversion of Lm_nn's
Ek=Lm_11*Lm_22-Lm_12*Lm_21
B_22=Lm_11/Ek
B_12=-Lm_12/Ek
B_21=-Lm_21/Ek
B_11=Lm_22/Ek
'
'
'
'   ...
'
For I=1 To Ord
    ...
Next I
'
'
```

UNITED STATES PATENT AND TRADEMARK OFFICE
CERTIFICATE OF CORRECTION

PATENT NO. : 5,211,179          p. 18 of 19
DATED : May 18, 1993
INVENTOR(S) : Dr. Ralph Haberl et al.

It is certified that error appears in the above-indentified patent and that said Letters Patent is hereby corrected as shown below:

```
'___ End of recursion
'
'
'
'Restorage of coefficients
For I=1 to Ord-1
   Fpe2(I+1)=Fd(Ord-I)
Next I
Mat Fd(1:Ord)=Fpe2(1:Ord)
Fd(0)=1
'
'___ End of coefficient calculation,
'___ Coefficients are entered in Fd(*) field
'    (Stability test possible for the coefficients)
'    Editing for transfer of field to FFT
'
'___ Calculation of spectrum
'    Transfer to FFT
'
'XA, YA : auxiliary fields of FFT
'
Fft_Size=512
'
CALL FFT(XA, YA, Fd, Fft_Size)
'
Prod=(Ene/SegSize)^2
L=Fft_Size DIV 2
'
```

UNITED STATES PATENT AND TRADEMARK OFFICE
CERTIFICATE OF CORRECTION

PATENT NO. : 5,211,179
DATED : May 18, 1993
INVENTOR(S) : Dr. Ralph Haberl, et al.

It is certified that error appears in the above-indentified patent and that said Letters Patent is hereby corrected as shown below:

```
,___ Spectrum AFB(*)
,
FOR I=1 TO L
   AFB(I)=Prod/(XA(I)^2+YA(I)^2)
NEXT I
,
, *** End ***
```

Signed and Sealed this

Thirteenth Day of December, 1994

BRUCE LEHMAN

Attest:

Attesting Officer

Commissioner of Patents and Trademarks